United States Patent [19]

Millar et al.

[11] 4,110,081

[45] Aug. 29, 1978

[54] MOVING-BED RADIAL FLOW SOLIDS-FLUID CONTACTING APPARATUS

[75] Inventors: Robert F. Millar, McCook; Paul J. Persico, Bolingbrook; Robert H. Jensen, Clarendon Hills, all of Ill.

[73] Assignee: UOP Inc., Des Plaines, Ill.

[21] Appl. No.: 805,062

[22] Filed: Jun. 9, 1977

[51] Int. Cl.² .................... B01J 8/12; B65G 65/30
[52] U.S. Cl. .................... 23/288 G; 23/288 B; 55/479; 208/165; 208/171; 210/189; 210/269; 214/17 R
[58] Field of Search .................... 23/288 G, 288 B, 283, 23/284; 208/152, 165, 171; 252/411 R, 415, 418; 210/31 R, 33, 189, 268, 269; 55/79, 390, 474, 479; 134/25 R; 214/17 R, 17 A

[56] References Cited

U.S. PATENT DOCUMENTS

| 2,546,625 | 3/1951 | Bergstrom | 208/171 X |
| 2,741,547 | 4/1956 | Alleman | 23/288 G |
| 3,854,887 | 12/1974 | Heinze et al. | 23/288 G |
| 3,883,312 | 5/1975 | Youngman | 23/288 G |
| 3,893,812 | 7/1975 | Conner et al. | 23/288 B |
| 3,917,458 | 11/1975 | Polak | 55/390 X |

*Primary Examiner*—Joseph Scovronek
*Attorney, Agent, or Firm*—James R. Hoatson, Jr.; John F. Spears, Jr.; William H. Page, II

[57] ABSTRACT

An improved radial flow moving bed reactor, or other type of fluid-solid contacting vessel, in which stagnant catalyst volumes are reduced. The improvement results from the placement of a plurality of catalyst collection scoops or a single discoid cover plate just above the catalyst withdrawal conduits in a manner which directs the removal of catalyst through an annular opening adjacent the inner catalyst retention screen.

6 Claims, 6 Drawing Figures

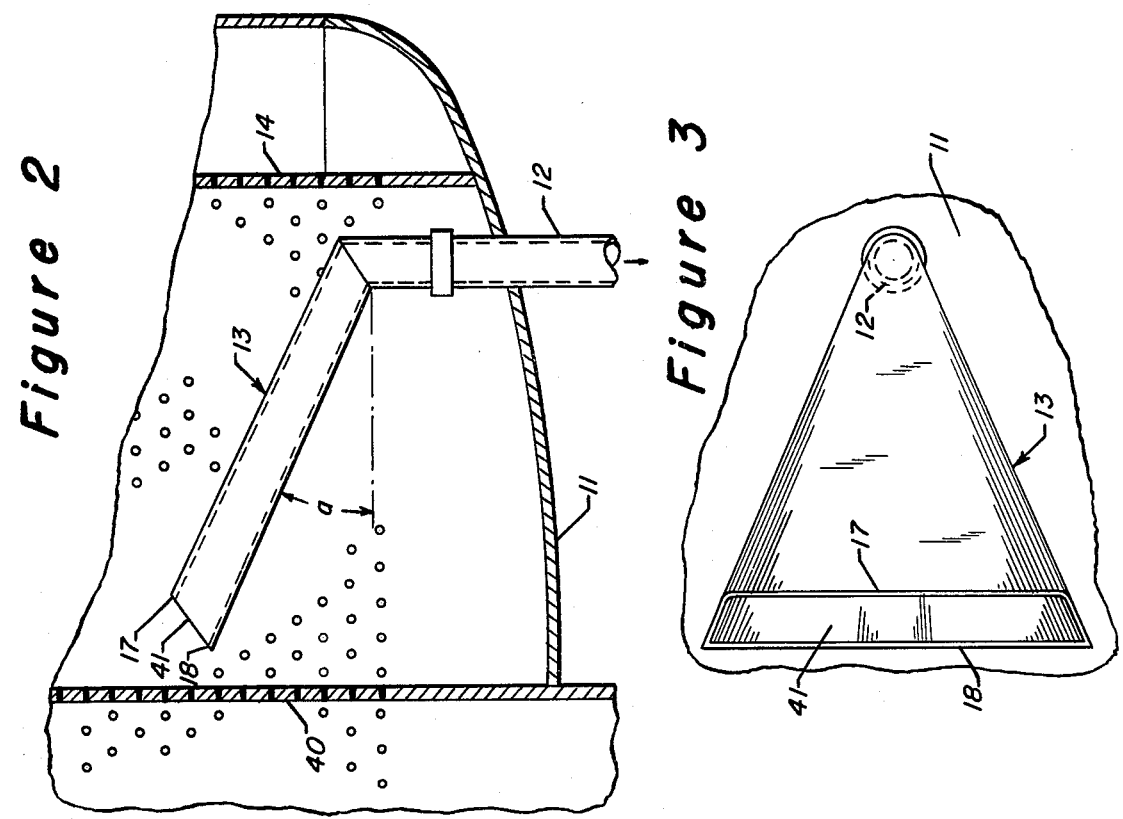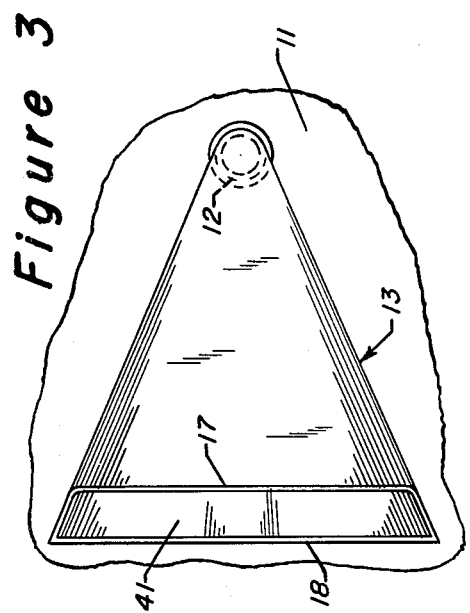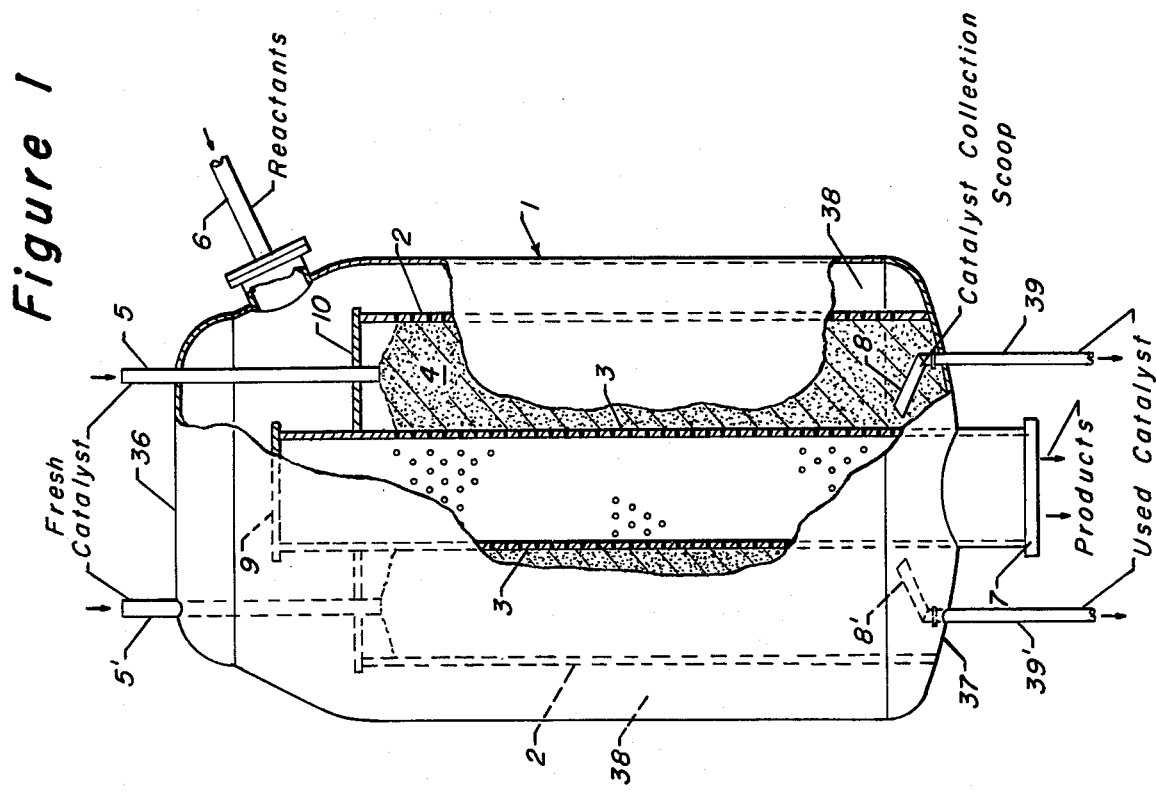

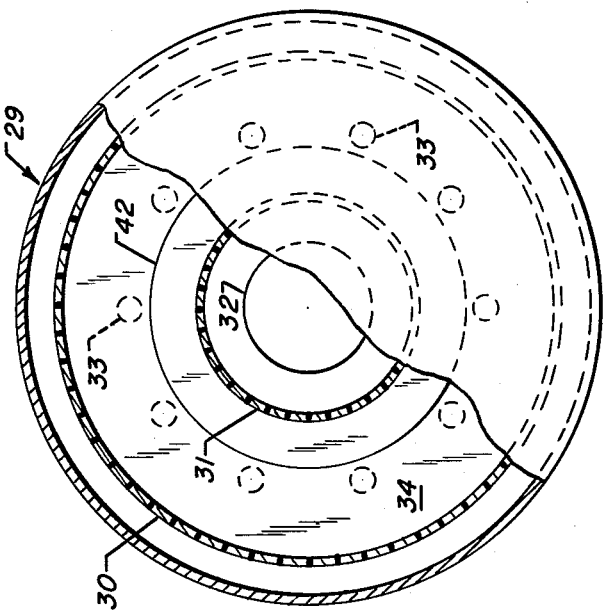
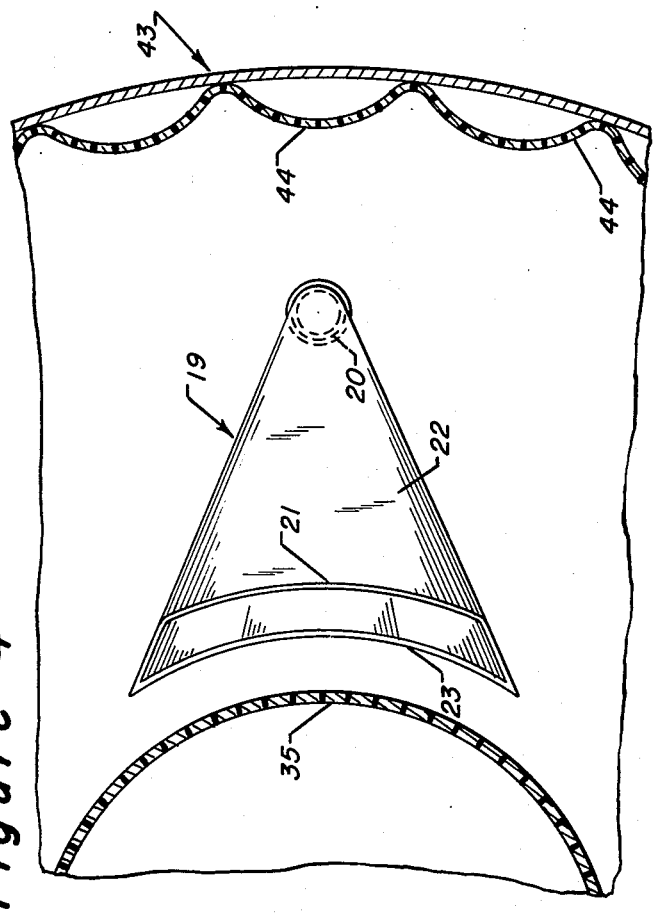
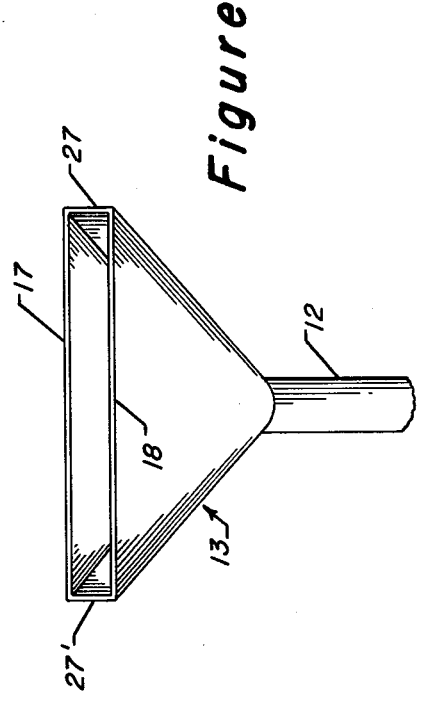

MOVING-BED RADIAL FLOW SOLIDS-FLUID CONTACTING APPARATUS

FIELD OF THE INVENTION

The invention relates to the design of vapor-solid contacting equipment and particularly to the design or reactors for use in hydrocarbon conversion processes. More specifically the invention relates to moving bed radial flow reactors used in vapor phase hydrocarbon conversion processes such as reforming, isomerization or dehydrogenation. It more particularly relates to the design of catalyst withdrawal systems for use on moving bed radial flow reactors. The invention therefore relates to apparatus similar in nature to those found in Class 23-288.

PRIOR ART

Fluid-solid contactors using an annular particle bed, that is a particle bed held in place by two concentric cylindrical particle retaining screens are in widespread commercial use and are well known in the art. It is also well-established in the art to utilize this type of apparatus as a moving bed reactor. This is shown, for instance, by U.S. Pat. Nos. 3,927,987 (Cl. 23-288); 3,907,511; 3,882,015; 3,799,866 (Cl. 208-139) and 3,692,496.

It is believed that heretofore the catalyst withdrawal systems employed at the bottom of the catalyst bed have attempted to achieve uniform catalyst flow through the use of centrally located catalyst passages. Typically these have consisted of a number of catalyst withdrawal conduits located intermediate the two catalyst retention screens, with the upper end of each conduit being covered by a conical cap designed to allow equal catalyst flow from every direction. This is shown in U.S. Pat. Nos. 3,706,536 (Cl. 23-288); 3,785,963 (Cl. 208-171) and 3,854,887. These three references present a great many details of the construction of moving bed reactors and illustrate that those skilled in the art are capable of utilizing the subject invention with a minimum of instruction.

BRIEF SUMMARY OF THE INVENTION

The invention provides a moving bed radial flow reactor or other type of contacting vessel having more uniform catalyst movement characteristics and a minimum amount of stagnant catalyst. This improvement is achieved through the use of either of two dissimilar catalyst withdrawal systems. A broad embodiment of the preferred system may be described as a radial flow moving bed reactor which comprises a vertically oriented cylindrical outer vessel; an outer first and an inner second cylindrical catalyst retention screen which are concentric with the central vertical axis of the outer vessel to provide an annular reactant distribution volume between the first screen and the inner surface of the vessel, an annular catalyst retention volume between the screens and a cylindrical reactant collection volume within the inner screen; catalyst inlet conduits communicating with the upper end of the catalyst retention volume; a reactant inlet conduit communicating with the reactant distribution volume; a reactant outlet conduit communicating with the reactant collection volume; a plurality of catalyst withdrawal conduits communicating with the lower end of the catalyst retention volume and an equal number of catalyst collection scoops having a lower end attached to an upper unsealed end of a catalyst withdrawal conduit and an open upper end which faces the second screen, with each scoop having a larger cross-sectional area at its upper end and reposing at an angle of about 15°–60° above horizontal, whereby catalyst is removed from the reactor through the catalyst collection scoops at points adjacent the inner second screen through an annular shaped vertical catalyst passageway.

DESCRIPTION OF THE DRAWING

FIG. 1 presents a vertical cross-sectional view of a moving bed radial flow reactor using the preferred catalyst collection scoops to achieve the desired catalyst flow pattern.

FIG. 2 is an enlarged view of a catalyst collection scoop as it is installed in a reactor.

FIG. 3 is the view seen looking downward on one configuration of the catalyst collection scoops.

FIG. 4 is the view seen looking downward toward a catalyst collection scoop having the preferred configuration.

FIG. 5 is the view seen looking horizontally toward the open upper end of a catalyst collection scoop.

FIG. 6 is a cross-sectional view looking downward on a reactor having a single cover plate instead of the preferred catalyst collection scoops.

Referring now to FIG. 1, there is shown a moving bed radial flow reactor formed in part by the outer vessel 1 and which conforms to the preferred embodiment of the invention. This vessel is a vertically oriented cylinder enclosed by upper end section 36 and lower end section or cap 37. A first or outer catalyst retention screen 2 is also cylindrical in shape, as is the inner or second catalyst retention screen 3. Both of these screens are concentric about the central vertical axis of the reactor. The outer surface of the first screen and the cylindrical inner surface of the outer vessel define an annular fluid or reactant distribution volume 38, into which the reactants flow from inlet conduit 6. An annular shaped bed of catalyst 4 is retained between the two screens. This catalyst bed is intermittently replenished with fresh catalyst which falls through catalyst inlet conduits 5 and 5'. For simplicity only two catalyst inlet conduits are shown; normally at least about eight are used. The top of the porous portion of each screen is preferably below the upper inner surface of the vessel, and the top of the catalyst bed is sealed off by an imperforate disk-shaped plate 10.

The reactants pass inward through the catalyst bed and enter the cylindrical fluid or reactant collection volume. The reactants and reaction products are then removed from the reactor through the reactant outlet conduit 7. The top of the reactant collection volume is sealed with a circular cover plate 9. The used catalyst is withdrawn from the reactor through a plurality of catalyst collection scoops represented by scoops 8 and 8'. Each scoop has an open upper end which faces the inner catalyst retention screen. The catalyst enters through this upper end and is therefore withdrawn in an annular pattern much closer to the inner screen than the outer screen. Each scoop has a lower end connected to a catalyst withdrawal conduit such as 39 and 30'. These conduits encircle the inner screen and pass through the lower end section 37. The catalyst collection scoops and the upper portion of the catalyst withdrawal conduits are filled with catalyst during operation of the reactor. This description of the preferred application of the invention is not intended to limit the apparatus to use as a reactor.

In FIG. 2, a side view of a catalyst collection scoop 13 is shown in greater detail. The lower end of the scoop is attached to a catalyst withdrawal conduit 12. This vertical conduit extends through the horizontal outer wall 11 of the reactor to a series of valves or a catalyst collection hopper as the case may be. Alternatively, the conduit may directly feed catalyst to another reactor in a "stacked" reactor design. The scoop is positioned such that opening 41 at the upper end of the scoop faces the inner catalyst retention screen 40 and is adjacent this screen. The opening therefore faces radially inward. The outer catalyst retention screen 14 is close to the lower end of the scoop. For simplicity, only a few of the large number of perforations in the screen are illustrated. As shown, the scoop is preferably formed by parallel, planar upper and lower imperforate panels. These panels have an angle "a" above horizontal as measured from the lower end of the scoop. The sides of the scoop are enclosed by opposing planar side walls.

In FIG. 3, the view seen when looking downward at a catalyst collection scoop 13 is presented. This scoop is similar to that shown in FIG. 2. The lower end of the scoop covers the open upper end of the catalyst withdrawal conduit 12. The upper panel of the scoop has an upper edge 17 which is spaced farther from the inner catalyst retention screen than the upper edge 18 of the lower panel. The triangular shaped panels result in the scoop having a larger cross-sectional area at its upper end than at its lower end.

FIG. 4 illustrates the preferred arcuate shape of the panel edges forming the upper end of a catalyst collection scoop 19. Again, the lower end of the scoop is positioned to direct catalyst into the withdrawal conduit 20. The upper edges of the panels are once again horizontally staggered to collect catalyst, with upper edge 21 being positioned farther from the inner catalyst retention screen 35 than the lower panel edge 23. In the preferred embodiment the upper edge of the upper panel 22 and of the lower panel are arcuate and have a radius of curvature which is correlated to that of the inner screen such that the distance measured radially between the inner screen and either edge is uniform at all points along each edge as shown. This view also shows the use of a scalloped outer catalyst screen 44 adjacent the cylindrical outer wall 43 of the reactor.

In FIG. 5 the view seen looking toward the upper open end of a catalyst collection scoop 13 is presented. This scoop is similar to those shown in FIGS. 2 and 3 rather than the arcuated edged scoop of FIG. 4. The lower end of the scoop is attached to a catalyst withdrawal conduit 12. The edge 17 of the upper panel is connected to the edge 18 of the lower panel by opposing, vertical, imperforate side walls 27 and 27'. The open upper end of the scoop is therefore circumscribed by elements 17, 18, 27 and 27'.

FIG. 6 illustrates a different embodiment of the invention. It is a cross-section taken through a vertical midpoint of a radial flow moving bed reactor and is the view seen looking downward toward the fluid or reactant outlet 32 at the bottom of the reactor. The cylindrical wall of the vessel 29 encloses an annular fluid distribution volume located between the cylindrical wall and the outer catalyst retention screen 30. This outer screen is concentric with the inner catalyst retention screen 31 and these two screens define the annular catalyst retention volume. A plurality of catalyst withdrawal conduits 33 communicate with the lower end of the catalyst retention volume. These conduits encircle the inner screen as shown. The open upper ends of the catalyst withdrawal conduits are dotted since they are located under a discoid cover plate 34. This unitary cover plate performs the same function as the previously described catalyst or particle collection scoops. The catalyst is withdrawn from the reactor through an annular catalyst passageway between the inner screen 31 and the circular inner edge 42 of the cover plate. The cover plate extends to outer screen 30 and is located at about the same elevation as the upper end of the catalyst collection scoops.

DETAILED DESCRIPTION

Radial flow fluid-solids contacting apparatus may be used in a wide variety of industrial processes. Examples are the radial flow reactors used in a variety of hydrocarbon conversion processes. These processes include the isomerization of normal paraffins, the dehydrogenation of normal paraffins and reforming of naphtha boiling range petroleum fractions. As is well known, in a radial flow reactor the various reactants flow along radials extending from the major central axis of the reactor to its periphery. The subject apparatus is directed to those reactors in which the reactant flow is inward. That is, the reactants flow inward from the annular reactant distribution volume to a cylindrical reactant collection volume. This central reactant collection volume is enclosed by the inner catalyst retention screen, which is commonly referred to as the centerpipe of the reactor. Radial flow may also be used in other contacting apparatus such as adsorbent chambers and treaters. As a corollary to its use as a moving bed reactor the subject apparatus may be used as a moving bed regenerator for the decarbonization, reduction or halogenation of used catalyst or adsorbents.

The invention is further restricted in that it is limited to moving bed fluid-solids contactors, such as moving bed reactors. The term "moving bed" as it is used herein is intended to refer to a particulate-containing system in which the particles rest upon one another in a dense bed and the inventory of the bed is gradually replaced through the removal of used particles at the bottom and the addition of fresh or regenerated particles at the top. The subject invention is therefore not directed to ebullated or fluidized bed contacting apparatus. The apparatus may be used with either vapor or liquid phase fluids.

It is believed that heretofore the particles have been withdrawn from annular beds through a number of centrally located openings at the bottom of the vessel. Centrally located is used in this context to indicate the particle or catalyst withdrawal conduits are located approximately midway the two particle retention screens or within the middle 50% of the distance between the screens. The outlet conduit was often covered by a cap or inverted cone such as shown in the previously cited references. The reason for utilizing these caps and the central placement of the withdrawal conduits was to promote a uniform withdrawal of particles from all parts of the bed. That is, it was hoped this prior art structure would effect the withdrawal of the particles adjacent both screens at equal rates.

Unfortunately, experience has indicated that these prior art systems do not achieve uniform catalyst withdrawal. Rather, they may leave a sizable amount of catalyst or particles in place within the apparatus. This stagnant material eventually becomes ineffective in its specific function and exerts a detrimental influence on the performance of the equipment. More specifically, it has been discovered that a large amount of particulate "pinning" may occur in the lower portion of the vessel, especially at higher vapor or liquid velocities through the particle bed. This is the formation of a stagnant layer of particles adjacent the inner retention screen. Undoubtedly, this is caused at least in part by the inward vapor flow. The stagnant material is normally in a sharply tapered triangular cross-section zone having a base at the bottom of the vessel and a hypotenuse angling upward toward the centerpipe.

There is a second undesirable effect which has been observed using the prior art particle withdrawal systems. This is the accumulation of particle fines caused by the normal movement-induced attrition of the particulate material in the zone of stagnant particles. These fines are moved toward the stagnant zone by the inward vapor flow but are not removed as would occur if this stagnant zone did not exist. Eventually this seals a number of small vapor passageways and causes a higher pressure drop across the bottom of the particle bed than at the top. This in turn distorts the desired equal flow rate through all parts of the annular particle bed. In a reactor this results in the actual space velocity being higher at the top of the reactor than at the bottom.

It is an objective of this invention to provide a moving bed radial flow solids-fluid contact apparatus. It is a further objective to provide a moving bed radial flow reactor having a minimum of stagnant catalyst and which lessens the accumulation of stagnant catalyst against the surface of the centerpipe during inward vapor flow.

The particulate matter used in the apparatus is preferably a hydrocarbon conversion catalyst, but it may be an adsorbent including activated carbon, a zeolite or an alumina as may be used to treat gas streams for the removal of water, sulfur compounds or halogen-containing chemicals. The particulate material may also be a solid acceptor used for the removal of sulfur oxides from a flue gas stream as disclosed in U.S. Pat. Nos. 3,776,854 and 3,832,445. Preferably, the particulate matter is spherical and has a diameter within the range of about 1/16-inch to ½-inch (0.15-1.25 cm). The words "catalyst" and "particle" are used interchangeably in many instances herein when referring to various elements of the apparatus. The use of either word is not intended to limit the application of function of these elements in a manner which unduly limits the invention. Catalyst used in the apparatus will preferably comprise an inorganic oxide support, such as alumina or silica, with a catalytically effective amount of a metal or metal oxide. The metal may be one or more chosen from the following group: nickel, cobalt, iron, platinum, tin, palladium, manganese or magnesium. The preparation of suitable adsorbents, acceptors and catalyst is well known to those skilled in the art and they may be of customary composition.

The outer vessel is preferably made of a suitable metal such as carbon or stainless steel, but may be formed from other materials including fiber reinforced plastics if the conditions of temperature, pressure, etc., allow their use. This vessel is to be constructed to meet the customary pressure vessel standards or other codes as may be applicable. The outer vessel is divided into upper and lower sections by a horizontal plane passing through a point equidistant the upper and lower horizontal inner surfaces, or their equivalents, located at the respective upper and lower ends of the vessel.

The two particle or catalyst retention screens are preferably fabricated using wedge-shape wire having a cross-section which decreases in the direction that is away from the particle side of the screen. This results in a self cleaning surface such that as any particles, or pieces thereof, pass through the openings between the screens they may fall free of the screen on the other side. Preferably, the wedge-shaped wires are aligned vertically to minimize catalyst attrition as the catalyst moves downward against the screen. The width of the reactant distribution volume, the distance between the screens and the diameter of the centerpipe may be as is customary in the art. The amount of particulate material, the thickness of the particle bed and the rate of fluid flow through the bed will be determined by such factors as the flow rate of the fluid stream, the capacity or activity of the particulate material, the desired WHSV, etc. Those skilled in the art are well versed in sizing these components of the apparatus, and the appropriate size will depend on the specific situation. The outer particle retention screen may be either cylindrical to provide an annular fluid distribution volume or it may be a scalloped screen as shown in FIG. 4.

The contact apparatus will be provided with a plurality of particle inlet conduits which pass through the upper section of the outer vessel and communicate with the top of the annular particle retention volume. About 6-10 inlet conduits are normally adequate to give proper distribution of the particulate material. The retention screens preferably have an imperforate section at the top to provide a seal which prevents any portion of the fluid stream from passing over the particle bed through possible void spaces. The screens may be capped as shown in FIG. 1 or they may be extended upward to the inner surface of the vessel as shown in several of the prior art references. The inlet conduits will normally be connected to a valve for controlling the rate of particle addition or directly to a hopper vessel used to distribute the particles. Alternately the inlet conduits may be connected to the outlet conduits of vessels (reactors) located above as in a stacked design.

There are two basic embodiments to the subject apparatus. Both are designed to effect the removal of the particulate material in an annular pattern adjacent the inner particle retention screen. In the preferred embodiment the apparatus comprises a plurality of particle collection scoops which are arranged around the bottom of the centerpipe in a circular pattern. Preferably, the tips of adjacent scoops come together or in close proximity (within 15 cm) of each other to form an annular catalyst collection area which is uniformly disposed about the centerpipe. The width of this zone, which is the same as the distance between the centerpipe and the upper edge of the respective scoop preferably should be less than 30 centimeters. Preferably the distance for the upper edge is less than 10 centimeters and is less than 5 centimeters for the lower edge when arcuate scoops are used. An average distance is specified since the straight edge scoops, such as shown in FIG. 3, will result in a varying distance. Preferably, the upper and lower edge of the scoop panels are arcuate and conform to the curvature of the centerpipe to present a uniform distance between the scoop and the centerpipe. Other edge shapes not shown may also be employed if desired.

The individual scoop are hollowform. That is, they are not solid but have a void interior space which conforms to their outer shape. Preferably, the upper and lower panels and side walls which enclose the scoops are imperforate. These elements of the scoops may be relatively porous, however, as to provide for drainage or vapor circulation. This may be desired in some cases to prevent coking or the entrapment of liquids in the particle withdrawal conduits. The cross-sectional area of the interior of each scoop is larger at the upper end which faces the centerpipe than at the lower end which is attached to the particle withdrawal outlet. The scoops are in this regard funnel-like particle collectors. To aid in the collection of the particles the lower edge of the scoop (the upper horizontal edge of the lower panel) is located closer to the centerpipe than the upper edge. This is shown in FIGS. 2 and 3 and enables the scoops to "catch" the descending particles.

The particle collection scoops, or catalyst collection scoops if the apparatus is used as a reactor, are inclined at an angle of from about 5°-60° above horizontal. This is measured as the angle "a" of FIG. 2. A preferred range for this angle is from 15°-45°, with 30° being particularly preferred. It is preferred that the upper and lower panels of the scoop are parallel and therefore have the same angle. This is not a necessity and the scoops may taper vertically also. The scoops may be surrounded by the same particulate material which is moved through the apparatus, or inert spacers such as ceramic spheres may be placed in the bottom of the vessel. Several supports may be placed around and under the scoops to prevent their movement and distortion during the operation of the apparatus.

The preferred embodiment of the invention may therefore be characterized as a reactor for the catalytic conversion of hydrocarbons which comprises a vertically oriented vessel having an internal volume located within a cylindrical side wall having an inner surface, the outer vessel being divided into upper and lower sections; a first vertically oriented catalyst retaining screen located within the outer vessel a distance radially inward from the outer surface of the inner surface of the outer vessel and defining an annular reactant distribution volume between the first catalyst retaining screen and the outer vessel; a second vertically oriented catalyst retaining screen located within the first catalyst retaining screen a distance radially inward from the first catalyst retaining screen and defining an annular catalyst retention volume having an upper and a lower end and located between the first and the second catalyst retaining screens and also defining a cylindrical reactant collection volume located within the second catalyst retaining screen; a plurality of catalyst inlet conduits located in the upper section of the outer vessel and communicating with the upper end of the annular catalyst retention volume; a reactant inlet means communicating with the annular reactant distribution volume; a reactant outlet means communicating with the cylindrical reactant collection volume; and, a catalyst withdrawal means located between the first and the second catalyst retention screens at the lower end of the annular catalyst retention volume, with the catalyst withdrawal means comprising: (i) a plurality of tubular catalyst withdrawal conduits distributed in a circular pattern encircling the second catalyst retention screen, each catalyst withdrawal conduit having an unsealed upper end which communicates with the annular catalyst retention volume; and, (ii) a plurality of hollow catalyst collection scoops, each scoop having an open upper first end which faces the second catalyst retention screen and a lower second end which is attached to the upper end of a catalyst withdrawal conduit, with one catalyst collection scoop being positioned over each of the catalyst withdrawal conduits, and with each catalyst collection scoop having a greater cross-sectional area at the upper first end than at the lower second end and reposing at an angle of from about 15°-45° above horizontal, with the upper first end of the catalyst collection scoops having upper and lower arcuate edges which are substantially uniformly spaced from the second catalyst retention screen to provide an annular vertical catalyst passageway.

In the other major embodiment, the particle withdrawal passageway at the bottom of the particle bed is an annular opening between the outer surface of the centerpipe and the inner edge of a unitary discoid cover plate. This embodiment is shown in FIG. 6. All elements of this embodiment are similar to those of the preferred embodiment except for the particle collection scoops which are replaced by the cover plate. The cover plate will preferably be fabricated within the vessel from several smaller pieces which may overlap or may be welded together. As shown in the Drawing, the cover plate has an outer circular edge which abuts the inner surface of the outer particle retention screen. The outer edge may rest on a circular lip extending inward from the outer screen in a manner which allows for expansion and contraction due to temperature changes. The remainder of the cover plate is supported either by vertical braces extending downward to the horizontal inner surface of the vessel or by horizontal ribs extending across the annular particle withdrawal passageway. The width of this passageway is preferably in the range of 3-15 centimeters. The cover plate may be imperforate or may be adapted for the vertical passage of vapors or liquids. It is therefore may be fabricated from the same screen material used to form the particle retention screens or from a solid metal plate of the appropriate thickness. Rigidity of the cover plate is maintained by various horizontal members, and its construction may be detailed by those skilled in the art of vessel or reactor design.

The discoid cover plate of this embodiment preferably has a horizontal upper and lower surface. It may however be slanted downward slightly in the direction of the centerpipe. The lower surface of the coverplate is preferably about 12-42 centimeters above the open and exposed under ends of the catalyst withdrawal conduits. There is no cone-shaped particle flow directing cap or other obstruction placed above the open ends of the conduit in the space between these open ends and the under side of the cover plate. This may result in some volumes of stagnant particles being maintained below the cover plate. However, experiments have indicated the particle withdrawal from the bed above the plate is uniform, and this is the important criterion. It has also been observed that this and the preferred embodiments are effective at circulating the particles adjacent the outer particle retention screen. This results from an unexpectedly large horizontal movement of the particles in an inward direction at the bottom of the annular particle bed. The residence time of the particles is therefore relatively uniform as compared to the prior art.

We claim as our invention:

1. A radial flow moving bed contact apparatus which comprises:
  (a) a vertically oriented vessel having an internal volume located within a cylindrical side wall having an inner surface, the outer vessel having upper and lower sections;

(b) a first vertically oriented particle retaining screen located within the outer vessel a distance radially inward from the inner surface of the outer vessel and defining a fluid distribution volume between the first particle retaining screen and the outer vessel;

(c) a second vertically oriented particle retaining screen located within the first particle retaining screen a distance radially inward from the first particle retaining screen and defining an annular particle retention volume having an upper and a lower end and located between the first and the second particle retaining screens and also defining a cylindrical fluid collection volume located within the second particle retaining screen;

(d) a plurality of particle inlet conduits located in the upper section of the outer vessel and communicating with the upper end of the annular particle retention volume;

(e) a fluid inlet means communicating with the fluid distribution volume;

(f) a fluid outlet means communicating with the cylindrical fluid collection volume; and, (g) a particle withdrawal means located between the first and the second particle retention screens at the lower end of the annular particle retention volume, the particle withdrawal means comprising:

(i) a plurality of vertical tubular particle withdrawal conduits distributed in a circular pattern encircling the second particle retention screen, each particle withdrawal conduit having an unsealed upper end which communicates with the annular particle retention volume; and, (ii) a plurality of particle collection scoops, each scoop having an open upper first end which faces the second particle retention screen and a lower second end which is attached to the upper end of a particle withdrawal conduit, the upper first end of each particle collection scoop being located between the lower second end of the particle collection scoop and the second particle-retaining screen, with one particle collection scoop being positioned over each of the particle withdrawal conduits, each particle collection scoop having a greater cross-sectional area at the upper first end than at the lower second end, and with each particle collection scoop comprising vertically spaced apart upper and lower planar panels reposing at an angle of from about 50°–60° above horizontal.

2. The apparatus of claim 1 wherein the first particle retaining screen is cylindrical and the fluid distribution volume is annular.

3. The apparatus of claim 2 wherein the upper first end of the particle collection scoop has an upper arcuate edge which is substantially uniformly spaced from the second catalyst retention screen to provide an annular vertical particle passageway.

4. The apparatus of claim 3 wherein the particle collection scoop has an angle above horizontal of from 15°–45°.

5. A radial flow moving bed contact apparatus which comprises:

(a) a vertically oriented vessel having an internal volume located within a cylindrical side wall having an inner surface, the outer vessel having upper and lower sections;

(b) a first vertically oriented particle retaining screen located within the outer vessel a distance radially inward from the inner surface of the outer vessel and defining a fluid distribution volume between the first particle retaining screen and the outer vessel;

(c) a second vertically oriented particle retaining screen located within the first particle-retaining screen a distance radially inward from the first particle-retaining screen and defining an annular particle retention volume having an upper and a lower end and located between the first and the second particle-retaining screens and also defining a cylindrical fluid collection volume located within the second particle-retaining screen;

(d) a plurality of particle inlet conduits located in the upper section of the outer vessel and communicating with the upper end of the annular particle-retention volume;

(e) a fluid inlet means communicating with the fluid distribution volume;

(f) a fluid outlet means communicating with the cylindrical fluid collection volume; and (g) a particle withdrawal means located between the first and the second particle-retention volume, the particle withdrawal means comprising:

(i) a plurality of tubular particle withdrawal conduits distributed in a circular pattern encircling the first particle retention screen, each particle withdrawal conduit having an unsealed upper end which communicates with the annular particle-retention volume; and, (ii) a horizontally oriented discoid cover plate positioned above the lower end of the annular catalyst retention volume and above the upper end of the particle withdrawal conduits, the cover plate being unitary and encircling the second particle-retention screen, the cover plate having a circular inner edge which is spaced apart from the second particle-retention screen to provide an annular vertical particle passageway between the cover plate and the second particle-retention screen, the cover plate not contacting a particle withdrawal conduit, and the circular inner edge of the cover plate being located between the second particle-retention screen and the unsealed upper ends of the particle withdrawal conduits and with the cover plate having a circular outer edge which abuts the first particle-retention screen.

6. The apparatus of claim 5 wherein the first particle-retaining screen is cylindrical the fluid distribution volume is annular and the cover plate is planar and horizonal.

* * * * *